United States Patent [19]

Lorenz et al.

[11] Patent Number: 5,525,123
[45] Date of Patent: Jun. 11, 1996

[54] COMPOSITION FOR SIMULTANEOUS DYEING AND BRIGHTENING OF HUMAN HAIR

[75] Inventors: Heribert Lorenz, Gross-Bieberau; Daisuke Misu, Pfungstadt, both of Germany

[73] Assignee: Goldwell AC, Germany

[21] Appl. No.: 303,225

[22] Filed: Sep. 8, 1994

[30] Foreign Application Priority Data

Sep. 14, 1993 [DE] Germany ............... 43 31 136.9

[51] Int. Cl.$^6$ ............... A61K 7/13; C09B 67/00
[52] U.S. Cl. ............... 8/408; 8/406; 8/618; 8/620; 8/623; 8/624; 8/627; 8/628; 8/631; 8/634; 8/635
[58] Field of Search ............... 8/405, 406, 408, 8/602, 606, 614, 618, 620, 623, 624, 627, 628, 635, 634, 631

[56] References Cited

U.S. PATENT DOCUMENTS

| 5,006,127 | 4/1991 | Tennigkeit et al. | 8/408 |
| 5,131,911 | 7/1992 | Lang et al. | 8/408 |
| 5,318,599 | 6/1994 | Lorenz et al. | 8/408 |
| 5,356,439 | 10/1994 | Schultz et al. | 8/405 |

*Primary Examiner*—Paul Lieberman
*Assistant Examiner*—Caroline L. Dusheck

[57] ABSTRACT

This invention comprises a hair dyeing composition based on oxidation dyestuff precursors which dyes and brightens the hair containing, besides at least one developing and at least one coupling agent, at least one metal salt and at least one ammonium compound selected from the group ammonium chloride, ammonium sulfate, ammonium carbonate, ammonium bicarbonate, and ammonium carbamate, having a pH-value between 8 and 11, preferably from 9 to 10, after admixture with an oxidizing agent in the ready-to-use preparation.

7 Claims, No Drawings

COMPOSITION FOR SIMULTANEOUS DYEING AND BRIGHTENING OF HUMAN HAIR

This invention refers to a new hair dyeing composition based on oxidation dyestuff precursors containing at least one developing and at least one coupling agent and providing a faster dyeing process combined with a brightening effect compared with conventional hair dyeing preparations.

Customary hair dyeing compositions normally comprise at least one developing and at least one coupling agent and optionally contain other direct dyestuffs as shading agents. Before application onto human hair, they are mixed with diluted aqueous hydrogen peroxide solution. The processing time on the hair is about between 30 and 40 minutes to achieve a complete dyeing effect. It is, therefore, obvious that users of those hair dyes wish to diminish such processing time.

At the same time users frequently desire to get not only the hair dyed but also an enhanced brightness thereof.

This demand is solved by the present invention which relates to a hair dyeing composition comprising at least one developing and at least one coupling agent, wherein this hair dyeing composition also comprises certain catalysts to accelerate the oxidation reaction, and certain ammonium compounds, whereby the pH-value of the ready-to-use composition after admixture with peroxide is between 8 and 11, preferably between 9 and 10.

By application of this composition, not only a fast and complete hair dyeing is achieved but also visible brightening of the colored hair.

In detail, the hair dyeing and brightening composition according to the invention comprises about 0.001 to 2.5% by wt., preferably about 0.01 to 1% by wt., calculated to the total composition prior to the addition of the peroxide solution, of at least one compound selected from the group consisting of copper chloride ($CuCl_2$), copper sulfate ($CuSO_4$), cobalt chloride, cerium sulfate, cerium chloride, vanadium sulfate, potassium iodide, sodium iodide, lithium chloride, potassium dichromate, magnesium acetate, calcium chloride, calcium nitrate, barium nitrate, manganese dioxide ($MnO_2$), and (or) hydroquinone.

As a further essential compound the compositions according to the invention comprise at least one ammonium compound selected from the group consisting of ammonium chloride, ammonium carbonate, ammonium bicarbonate, ammonium sulfate, and (or) ammonium carbamate in a proportion of 0.5 to 10, preferably about 1 to 5% by wt., calculated to the total composition (excluding oxidizing agent).

European Patent Application No. 435 012 already discloses hair dyeing compositions comprising an $HCO_3^-$-ion forming substance and an alkali releasing substance to adjust the pH-value between 8.2 and 9.0 in a first phase, and a second phase comprising a hydrogen peroxide solution having a pH-value between 2.0 and 4.0, whereof the pH-value of the mixture of both phases is supposed to be between 6.5 and 7.9. These dyeing compositions do not achieve the effects intended with the hair dyeing and brightening compositions of the invention.

All oxidation dyestuff precursors known and useful for this purpose may be used as developing agents for the compositions according to the invention.

As such are mentioned in particular: 1,4-diaminobenzene, 2,5-diaminotoluene, 4-aminophenol, 2,5-diaminobenzyl alcohol, 1-amino-4-[bis(2-hydroxyethyl)-amino]benzene, 3-methyl-4-aminophenol, tetraaminopyrimidine, triaminohydroxypyrimidines, especially 2,5,6-triamino-4-hydroxypyrimidine, diaminodihydroxypyrimidines, especially 2,4-dihydroxy-5,6-diaminopyrimidine and 4,6-dihydroxy-2,5-diaminopyrimidine, and 2-(2'-hydroxyethylamino)-5-aminotoluene, and the soluble salts of these developing agents.

Obviously other developing agents may be used, too, solely or in admixture with each other, e.g., the well-known 5,6-dihydroxyindole and the derivatives thereof.

The proportion of the developing agent is about 0.05 to about 5% by wt., preferably 0.1 to 3, more preferred 0.25 to 1.5% by wt., calculated to the total composition of the preparation before admixture with the peroxide, and if present as a salt, calculated to the free base.

Preferred coupling substances, which are used in a molar ratio of developing agent to coupling agent between about 0.5:1 and about 2.5:1, are particularly resorcinol, 2-methylresorcinol, 4-chlororesorcinol, 2-aminophenol, 4-(N-methyl)aminophenol, 3-aminophenol, 3-N,N-dimethyl aminophenol, 4-amino-3-methyl phenol, 5-amino-2-methyl phenol, 6-amino-3-methyl phenol, 3-amino-2-methyl amino-6-methoxypyridine, 2-amino-3-hydroxypyridine, 4-aminodiphenyl amine, 4,4'-diaminodiphenyl amine, 2-dimethyl amino-5-aminopyridine, 2,6-diaminopyridine, 1,3-diaminobenzene, 1-ethoxy-2,4-diaminobenzene, 1-methoxy-2-amino-4(2-hydroxyethyl)aminobenzene, 1-amino-3-(2'-hydroxyethylamino)benzene, 1-amino-3-[bis(2'-hydroxyethyl)amino]benzene, 1,3-diaminotoluene, α-naphthol, 1,4-diamino-2-chlorobenzene, 4,6-dichlororesorcinol, 4-hydroxy-1,2-methylene dioxybenzene, 1,5-dihydroxynaphthaline, 1,7-dihydroxynaphthaline, 2,7-dihydroxynaphthaline, 1-hydroxynaphthaline, 2,4-diamino-3-chlorophenol, and (or) 1-methoxy-2-amino-4-(2'-hydroxyethylamino)benzene.

Obviously mixtures of different coupling substances may also be used to achieve particular color shades, especially those of resorcinol or 2-methylresorcinol with 2-aminophenol and (or) 3-aminophenol, of resorcinol or 2-methylresorcinol and 1-methoxy-2-amino-4-(2'-hydroxyethylamino)benzene, mixtures of 2-amino-3hydroxypyridine with 5-amino-2-methyl phenol and (or) 1-methoxy-2-amino-4-(2'-hydroxyethylamino)benzene, or 1,3-diaminobenzene with 1,4-diamino-2-chlorobenzene.

In order to achieve certain coloration shades, customary direct dyes may be included optionally, e.g., the known Arianor dyes, or also nitro dyes such as 2-amino-4,6-dinitrophenol, 2-amino-6-chloro-4-nitrophenol, 2-amino-4-nitrophenol, etc., as well as also known plant dyes, e.g., henna in low quantities, i.e. between 0.05 and 1% by wt.

Excluded is the additional use of 2-nitro-p-phenylene diamine and 4-nitro-o-phenylene dieunine due to their critical toxicity.

The total quantity of the dyeing mixture in the final product is preferably about 0.2 to about 6.0% by wt., particularly about 0.5 to about 4% by wt. of the hair dyeing composition.

For the production of the hair dyeing composition according to the invention, oxidation dyestuff presursors, i.e. the mixture of developing agent and coupling agent and optionally present direct dyestuffs as well as catalysts and ammonium compounds, are incorporated in acceptable cosmetc carriers. These are particularly emulsions like creams or gels.

Those compositions and further substances contained therein, particularly surface-active agents; stabilizers, thickening agents, etc. belong to the state of the art and are described in various monographies, e.g., K. Schrader, "Grundlagen und Rezepturen der Kosmetika", 2nd Ed., (1989, Hüthig Buchverlag), pp. 796 to 815. Therefore, reference is expressly made to this and other monographies.

The compositions according to the invention are mixed with peroxide containing substances, e.g., with a 6% hydrogen peroxide solution in equal proportions before application onto human hair, where they are left to act for about 10 to 20 minutes, preferably about 15 minutes, whereafter they are washed out with a usual shampoo.

The hydrogen peroxide compositions are preferably used per se, but may be replaced by other peroxide preparations, e.g., perborates, urea peroxide, melamin peroxide, etc. However, dosage and handling of such preparations may be more complicated, as they have to be kept anhydrous until application.

The following examples illustrate the invention.

EXAMPLES

Into a carrier comprising

| | |
|---|---|
| Cetylstearyl alcohol | 12.00% by wt. |
| Coconut monoethanolamide | 2.30 |
| Stearic acid monoethanolamide | 2.30 |
| Propylene glycol monostearate | 0.60 |
| Oleyl alcohol ethoxylate (5 EO) | 5.00 |
| Oleic acid | 2.50 |
| 1,2-Propanediol | 1.00 |
| Sodium laurylsulfate | 0.50 |
| Complexing agent (EDTA) | 0.50 |
| Sodium sulfite | 0.50 |
| Ascorbic acid | 0.30 |
| Protein hydrolyzate | 1.00 |
| Perfume | 0.40 |
| Ammonia (25%) | 8.00 |
| Water | @ 100.00 | the following mixtures were incorporated, specified by numbers 1 to 5 (quantities each in percent by weight, calculated to the total composition):

| No. 1 | |
|---|---|
| 2,5-Diamonotoluene sulfate | 0.75 |
| Resorcinol | 0.08 |
| 4-Chlororesorcinol | 0.25 |
| 3-Aminophenol | 0.05 |
| 5-Amino-2-methyl phenol | 0.02 |
| Calcium chloride | 0.10 |
| Ammonium chloride | 0.50 |

40 g of this dyeing cream are mixed with 40 ml of 6% aqueous hydrogen peroxide solution, applied onto strands of hair and left at 30° C. to process for 15 minutes.

After shampooing and drying, the dyeing result is an intense dark blonde hair color.

The omission of ammonium chloride resulted in a dull, less lustrous coloration; an omission of calcium chloride left the dyeing process incomplete within 15 minutes.

| No. 2 | |
|---|---|
| 2,5-Diaminotoluene sulfate | 0.75 |
| Resorcinol | 0.08 |
| 4-Chlororesorcinol | 0.25 |
| 3-Aminophenol | 0.05 |
| 5-Amino-2-methyl phenol | 0.02 |
| Hydroquinone | 0.50 |
| Ammonium hydrogen carbonate | 4.00 |

The dyeing was effected according to the procedure described in example No. 1, whereupon dark blonde hair with a bright lustre was obtained.

An omission of ammonium hydrogen carbonate resulted in a dull color image; an omission of hydroquinone did not result in a completed dyeing process within 15 minutes.

| No. 3 | |
|---|---|
| 2,5-Diaminotoluene sulfate | 0.75 |
| Resorcinol | 0.08 |
| 4-Chlororesorcinol | 0.25 |
| 3-Aminophenol | 0.05 |
| 5-Amino-2-methyl phenol | 0.02 |
| Potassium iodide | 0.02 |
| Ammonium chloride | 3.00 |

The procedure was the same as described in No. 1, whereupon again a bright dark-blonde coloration was obtained.

An omission of ammonium chloride resulted in a dull color; omission of the potassium iodide did not lead to a complete dyeing result within 15 minutes.

| No. 4 | |
|---|---|
| 2,5-Diaminotoluene sulfate | 0.54 |
| Resorcinol | 0.05 |
| 4-Chlororesorcinol | 0.20 |
| 3-Aminophenol | 0.02 |
| 5-Amino-2-methyl phenol | 0.01 |
| Potassium iodide | 0.02 |
| Ammonium sulfate | 1.00 |

The dyeing was performed according to the procedure described in No. 1.

A bright medium blonde shade was obtained.

An omission of ammonium sulfate resulted in a loss of the bright gloss; an omission of potassium iodide did not lead to a completed hair dyeing process within 15 minutes.

| No. 5 | |
|---|---|
| 2,5-Diamonotoluene sulfate | 0.90 |
| Resorcinol | 0.15 |
| 3-Aminophenol | 0.10 |
| 4-Aminophenol | 0.40 |
| 5-Amino-2-methyl phenol | 0.10 |
| Calcium chloride | 0.30 |
| Ammonium carbamate | 2.00 |

The procedure as described in No. 1 was repeated; a bright light hazel hair shade was achieved.

An omission of ammonium carbamate resulted in a dull hair color; an omission of calcium chloride resulted in an incomplete dyeing process within 15 minutes.

We claim:

1. Composition for simultaneous dyeing and brightening of human hair, comprising at least one developing agent at least one coupling agent, and a mixture of
   (a) about 0.001 to about 2.5% by wt., calculated to the total composition excluding oxidizing agent, of at least one of the compounds selected from copper chloride, copper sulfate, potassium iodide, sodium iodide, calcium chloride, calcium nitrate, lithium chloride, magnesium acetate, potassium bichromate, barium nitrate, cobalt chloride, cerium sulfate, cerium chloride, vanadium sulfate, manganese dioxide, and/or hydroquinone, and
   (b) about 1 to about 10% by wt., calculated to the total composition excluding oxidizing agent, of at least one ammonium compound selected from ammonium chloride, ammonium sulfate, ammonium carbonate, ammonium bicarbonate, and ammonium carbamate, and (c) having a pH-value between 8.0 and 11 after admixture with peroxide.

2. Composition according to claim 1, comprising about 0.01 to about 1% by wt. of at least one of the compounds listed in (a).

3. Composition according to claim 1, comprising about 1 to 5% by wt. of one of the ammonium compounds listed in (b).

4. Composition according to claim 1, wherein said composition has a pH-value between 9 and 10 after admixture with peroxide.

5. Composition according to claim 2, comprising about 1 to 5% by wt. of one of the ammonium compounds listed in (b).

6. Composition according to claim 2, wherein said composition has a pH-value between 9 and 10 after admixture with peroxide.

7. Composition according to claim 3, wherein said composition has a pH-value between 9 and 10 after admixture with peroxide.

* * * * *

UNITED STATES PATENT AND TRADEMARK OFFICE
CERTIFICATE OF CORRECTION

PATENT NO.    :    5,525,123
DATED         :    June 11, 1996
INVENTOR(S)   :    Herbert Lorenz and Daisuke Misu It is certified that an error appears in the above-identified patent and that said Letters Patent is hereby corrected as shown below:

On the title page item [73] should read as follows:

[73] Assignee: Goldwell AG, Germany

Signed and Sealed this

Twenty-seventh Day of August, 1996

Attest:

BRUCE LEHMAN

*Attesting Officer*    *Commissioner of Patents and Trademarks*